United States Patent [19]
Shealy et al.

[11] 4,232,154
[45] Nov. 4, 1980

[54] CARBOCYCLIC ANALOGS OF CYTOSINE NUCLEOSIDES EXHIBITING ANTIVIRAL AND ANTINEOPLASTIC ACTIVITY

[75] Inventors: Y. Fulmer Shealy, Birmingham; C. Allen O'Dell, Fairfield, both of Ala.

[73] Assignee: United States of America, Washington, D.C.

[21] Appl. No.: 58,177

[22] Filed: Jul. 17, 1979

Related U.S. Application Data

[62] Division of Ser. No. 860,086, Dec. 13, 1977, Pat. No. 4,177,348.

[51] Int. Cl.$^2$ ............... C07D 239/46; C07D 498/04; A61K 31/505
[52] U.S. Cl. .................................................... 544/250
[58] Field of Search ........................................ 544/250

[56] References Cited

U.S. PATENT DOCUMENTS 3,040,026  6/1972  Duschinsky ..................... 544/317

FOREIGN PATENT DOCUMENTS 2038807  2/1971  Fed. Rep. of Germany .

OTHER PUBLICATIONS

Shealy et al.I,J.Pharm. Sci. 62, 1252 (1973).
Shealy et al. II, J. Pharm. Sci. 62, 858 (1973).
Shaeffer et al. I, J. Org. Chem. 25, 774 (1960).
Shealy et al. III, J. Amer. Chem. Sci. 91, 3075 (1969).
Kishi et al. Chem. Comm. 1967, 852.
Shealey et al. VI, Tet. Letters 1969, 2231-2234 (1969).
Shaeffer et al. II, J. Pharm. Sci. 53, 1510 (1964).
Shealey et al. V, J. Amer. Chem. Soc. 88, 3885 (1966).
Cook et al., J. Het. Chem. 15, 1-8 (1978).
Shealey et al. VI, J. Het. Chem. 10, p. 601 (1973).
Murdock et al. J. Amer. Chem. Soc. 84,3758 (1962).
Shealey et al. VII, J. Het. Chem. 13, 1015-1020 (1976).
Oxford Chem. Dictionery vol. 2, pp. 809, 837.
Shealey et al. VIII, Chem. Abs. 90, 39151h (1978).

*Primary Examiner*—Mark L. Berch
*Attorney, Agent, or Firm*—Holman & Stern

[57] ABSTRACT

Novel compounds are disclosed which are carbocyclic analogs of cytosine nucleosides in which the pentose moiety of the nucleoside is replaced by a cyclopentane ring. The novel compounds exhibit antiviral activity, and certain of them also exhibit antineoplastic activity against the L 1210 mouse leukemia test system.

1 Claim, No Drawings

CARBOCYCLIC ANALOGS OF CYTOSINE NUCLEOSIDES EXHIBITING ANTIVIRAL AND ANTINEOPLASTIC ACTIVITY

This is a divisional of application Ser. No. 860,086, filed Dec. 13, 1977, now U.S. Pat. No. 4,177,348.

BACKGROUND OF THE INVENTION

This invention relates to novel analogs of cytosine nucleosides and, more particularly, to carbocyclic analogs of cytosine nucleosides in which the pentose moiety of the nucleosides is replaced by a cyclopentane ring.

Cytosine nucleosides and their 5'-phosphates are involved essentially in the biosynthesis of nucleic acids and in other biochemical processes. Cytidine and 2'-deoxycytidine are nucleoside moieties of ribonucleic acid and deoxyribonucleic acid respectively. Because of the essential and intimate involvement of cytosine nucleosides in vital biochemical processes, structural analogs of these compounds are potentially important as chemotherapeutic agents.

Currently, the best known example of a therapeutically useful cytosine nucleoside is 1-$\beta$-D-arabinofuranosylcytosine, frequently designated by the acronym Ara-C. This compound has demonstrated antiviral and antineoplastic activity, as reviewed by Cohen, "Introduction to the Biochemistry of D-Arabinosyl Nucleosides", in *Progress in Nucleic Acid Research and Molecular Biology*, Vol. 5, Davidson and Cohn, Editors, Academic Press, New York, N.Y., 1966; and by Creasey, "Arabinosylcytosine", in *Antineoplastic and Immunosuppressive Agents*, Part II, Chapter 42, Sartorelli and Johns, Editors, Springer-Verlag, New York, N.Y., 1975.

Part of the molecule of cytosine nucleosides, including cytidine, 2'-deoxycytidine, and Ara-C, is a sugar (pentose) unit. The natural cytosine nucleosides and many of their analogs are subject to the action of enzymes (phosphorylases and hydrolases) which cleave the nucleosides to the sugar and pyrimidine moieties. Analogs of these nucleosides which are resistant to such enzyme cleavage may inhibit the action of certain enzymes that carry out biochemical reactions constituting the biosynthesis of nucleic acids, or they may inhibit the action of enzymes that interconvert the natural pyrimidine nucleotides. These inhibitory actions may exert profound effects on the metabolism of cells, which effects may be expressed as therapeutically useful activity.

Carbocyclic analogs of uracil nucleosides have previously been synthesized and described by Shealy and O'Dell, *Journal of Heterocyclic Chemistry*, Vol. 13, pp 1015-1020, October, 1976. No therapeutically useful activity was shown to be exhibited by such analogs.

SUMMARY OF THE INVENTION

The novel compounds of the present invention are carbocyclic analogs of cytosine nucleosides in which the pentose moiety of the nucleosides, i.e., the tetrahydrofuran ring thereof, is replaced by a cyclopentane ring. The novel compounds have a formula selected from the group consisting of

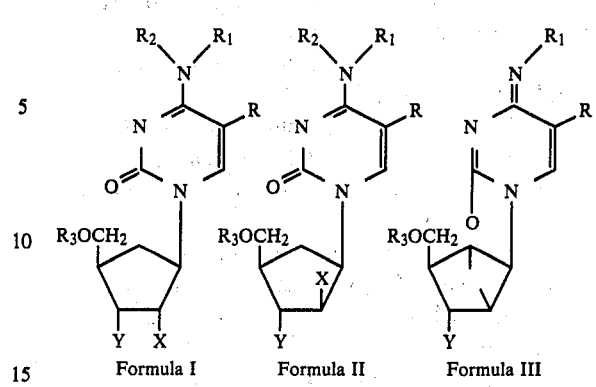

Formula I    Formula II    Formula III wherein X and Y are hydrogen, hydroxy or acyloxy; R is hydrogen, lower alkyl or halogen (including fluorine, chlorine, bromine or iodine); $R_1$ and $R_2$ are hydrogen or lower alkyl; and $R_3$ is hydrogen or acyl (including alkanoyl or aroyl).

The compounds represented by Formula I are carbocyclic analogs of the pyrimidine nucleosides cytidine, 2'-deoxycytidine, and 3'-deoxycytidine and of their derivatives and nucleoside analogs. The compounds of Formula II are carbocyclic analogs of 1-$\beta$-arabinofuranosylcytosine and its derivatives and nucleoside analogs. The compounds of Formula III are carbocyclic analogs of $O^2$, 2'-cyclocytidine and its derivatives and nucleoside analogs.

The carbocyclic analogs of the present invention are not subject to the action of enzymes (phosphorylases and hydrolases) that may cleave cytosine nucleosides, and exhibit therapeutically useful antiviral activity. The compounds of Formula I also exhibit antineoplastic activity against the L 1210 mouse leukemia test system. The compounds of Formula III furthermore have utility as intermediates in the synthesis of compounds of Formula II.

DESCRIPTION OF PREFERRED EMBODIMENTS

The carbocyclic analogs in accordance with the present invention are compounds having the same chemical structure as the corresponding nucleoside except that the oxygen atom of the furanose moiety of the nucleoside is replaced by a methylene group in the carbocyclic analog; or, differently expressed, in the carbocyclic analog a cyclopentane ring replaces the tetrahydrofuran ring of the corresponding nucleoside.

The preferred compounds of Formula I are those having the formula

Formula IV wherein X and Y are hydrogen or hydroxy; and $R_1$ and $R_2$ are hydrogen or lower alkyl.

Specifically preferred compounds encompassed by Formula IV include the following:

4-amino-1-[(1α,2β,3β,4α)-(±)-2,3-dihydroxy-4-(hydroxymethyl)cyclopentyl]-2(1H)-pyrimidinone (Formula IV, $R_1=R_2=H$; $X=Y=OH$) (the carbocyclic analog of cytidine)

4-amino-1-[(1α,3β,4α)-(±)-3-hydroxy-4-(hydroxymethyl)cyclopentyl]-2(1H)-pyrimidinone (Formula IV, $R_1=R_2=X=H$; $Y=OH$) (the carbocyclic analog of 2'-deoxycytidine);

4-amino-1-[(1α,2β,4α)-(±)-2-hydroxy-4-(hydroxymethyl)cyclopentyl]-2(1H)-pyrimidinone (Formula IV, $R_1=R_2=Y=H$; $X=OH$) (the carbocyclic analog of 3'-deoxycytidine);

1-[(1α,2β,3α,4α)-(±)-2,3-dihydroxy-4-(hydroxymethyl)cyclopentyl]-4-(dimethylamino)-2(1H)-pyrimidinone (Formula IV, $R_1=R_2=CH_3$; $X=Y=OH$) (the carbocyclic analog of N,N-dimethylcytidine);

4-(dimethylamino)1-[(1α,3β,4α)-(±)-3-hydroxy-4-(hydroxymethyl)cyclopentyl]-2(1H)-pyrimidinone (Formula IV, $R_1=R_2=CH_3$; $X=H$; $Y=OH$) (the carbocyclic analog of N,N-dimethyl-2'-deoxycytidine);

4-(dimethylamino)-1-[(1α,2β,4α)-(±)-2-hydroxy-4-(hydroxymethyl)cyclopentyl]-2(1H)-pyrimidinone (Formula IV, $R_1=R_2=CH_3$; $X=OH$, $Y=H$) (the carbocyclic analog of N,N-dimethyl-3'-deoxycytidine).

The preferred compounds of Formula II are those having the formula

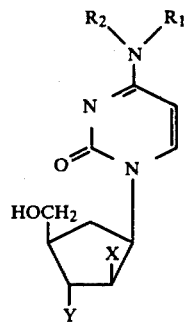

Formula V wherein X and Y are hydrogen or hydroxy; and $R_1$ and $R_2$ are hydrogen or lower alkyl.

Specifically preferred compounds encompassed by Formula V include the following:

4-amino-1-[(1α,2α,3β,4α)-(±)-2,3-dihydroxy-4-hydroxymethyl)cyclopentyl]-2(1H)-pyrimidinone (Formula, V, $R_1=R_2=H$; $X=Y=OH$) (the carbocyclic analog of 1-β-arabinofuranosylcytosine);

4-amino-1-[(1α,2α,4α)-(±)-2-hydroxy-4-(hydroxymethyl)cyclopentyl]-2(1H)-pyrimidinone (Formula V, $R_1=R_2=Y=H$; $X=OH$) (the carbocyclic analog of 3'-deoxy-1-β-arabinofuranosylcytosine).

The preferred compounds of Formula III are those having the formula

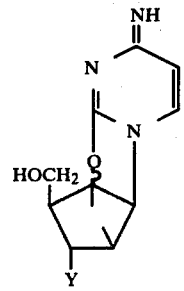

Formula VI wherein Y is hydrogen or hydroxy.

The compounds of Formula VI include the carbocyclic analog of $O^2,2'$-cyclocytidine ($Y=OH$); and the carbocyclic analog of $3'$-deoxy-$O^2,2'$-cyclocytidine($Y=H$).

The synthesis of the novel compounds of the present invention can be readily carried out employing, as starting materials, the corresponding carbocyclic analogs or uracil nucleosides, such as those described by Shealy and O'Dell, *Journal of Heterocyclic Chemistry*, Vol 13, pp 1015-1020 (1976). For example, for the synthesis of compounds of Formula I the starting material would be a carbocyclic analog of a uracil nucleoside having the formula

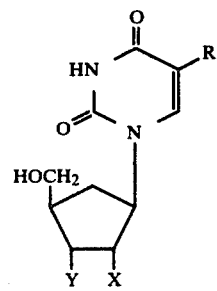

Formula VII wherein X and Y are hydrogen or hydroxy; and R is hydrogen, lower alkyl or halogen.

The first step in the synthesis is to protect the hydroxy groups of the carbocyclic analog of the uracil nucleoside, for example, by acyl groups such as the benzoyl group. Protection by an acyl group may be accomplished by acylating the hydroxy groups with a stoichiometric amount of an acylating agent such as an acyl halide or an acyl anhydride. Alternatively, a convenient procedure is to acylate with an excess amount of an acyl halide, thereby acylating the pyrimidine ring as well as the hydroxy groups, in order to ensure complete acylation of the hydroxy groups. The surplus acyl group on the pyridine ring may then be selectively removed in a weakly acidic solution, leaving the hydroxy groups protected.

The hydroxy-protected carbocyclic analog of a uracil nucleoside is then reacted with a reagent for replacing an oxo group of a heterocycle with a chloro group (e.g., a thionyl chloride-dimethylformamide reagent), so as to convert the analog to the 4-chloro-2(1H)-pyrimidinone derivative, having the formula

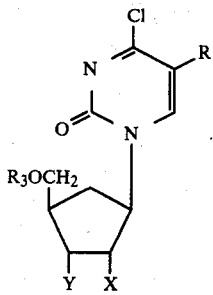

Formula VIII wherein R is as defined above, R₃ is acyl, and X and Y are hydrogen or acyloxy (the acyloxy group being the protected form of the hydroxy group defined by X and/or Y in Formula VII).

Treatment of the 4-chloro-2(1H)-pyrimidinone derivative with ammonia or an amine produces the desired carbocyclic analog of a cytosine nucleoside represented by Formula I. Use of a dialkyl amine, such as dimethylamine, results in $R_1$ and $R_2$ in Formula I being the corresponding alkyl group. When ammonia is used as the treating agent, and if the 4-chloro-2(1H)-pyrimidinone derivative has been purified, $R_1$ and $R_2$ will be hydrogen. When unpurified 4-chloro-2(1H)-pyrimidinone derivative is treated with ammonia, the carbocyclic analog of the N,N-dimethylcytosine nucleoside may be produced as a biproduct, the source of the dimethylamino group being the dimethylformamide used in the preparation of the 4-chloro-2(1H)-pyrimidinone derivative. In such case, the N,N-dimethylcytosine derivative may be separated from the cytosine derivative by ion-exchange chromatography.

The novel compounds of the present invention represented by Formula III can be prepared by treating a compound of Formula I wherein X is OH, with a reagent that effects elimination of a molecule of water between position 2 of the cycloptenane ring and position 2 of the pyrimidine ring accompanied by inversion of the configuration at position 2 of the cyclopentane ring. Examples of such reagents which effect this conversion are 2-acetoxybenzoyl chloride, or a thionyl chloride-dimethylformamide reagent, the latter being preferred.

The compounds of the present invention represented by Formula II can be prepared either from the analogous carbocyclic analogs of uracil nucleosides by a process similar to that described above for the preparation of compounds represented by Formula I; or by treating a compound represented by Formula III with a base such as aqueous ammonia.

The carbocyclic analogs of cytosine nucleosides in accordance with the present invention have antiviral activity and may be used in the treatment of various human viral diseases caused by both DNA viruses, such as herpes simplex virus Type 1 and vaccinia virus, and RNA viruses, such as rhinovirus Type 1A and influenza virus. Furthermore, the compounds represented by Formula I may be used in the treatment of animal tumors, as demonstrated by their antineoplastic activity against the L 1210 mouse leukemia test system. For such purposes, the compounds of the present invention are employed in the form of pharmaceutical compositions in a mixture with a pharmaceutically acceptable carrier, such as physiological saline or distilled water.

The invention is further illustrated by way of the following examples, wherein all temperatures are in degrees centigrade.

EXAMPLE 1

The Carbocyclic Analog of Cytidine (Formula IV, $R_1=R_2=H$; $X=Y=OH$).

A solution of benzoyl chloride (3.07 g.) in anhydrous pyridine (12.5 ml.) was added dropwise to a solution of 1-[(1d, 2β, 3β, 4α)-(±)-2,3-dihydroxy-4-(hydroxymethyl)cyclopentyl]-2,4(1H, 3H)-pyrimidinedione (Formula VII, R=H, X=Y=OH; the carbocyclic analog of uridine) (1.203 g.) in anhydrous pyridine (25 ml.). The solutions of the reactants and the reaction mixture were protected from atmospheric moisture, and the reaction mixture was stirred. The reaction was mildly exothermic; and, after the addition of benzoyl chloride had been completed, the reaction solution was heated at 57°–58° for 48 hr. The reaction solution was then cooled to room temperature and poured slowly into a water-ice mixture (500 ml.). The reaction vessel was rinsed twice with 3-ml. portions of pyridine, and these rinsings were added to the cold mixture. After the ice had melted, the mixture was filtered to separate a white solid that was washed thoroughly with water and dried under reduced pressure at room temperature: weight 3.18 g. (99% yield, calculated as the tetrabenzoyl derivative of the carbocyclic analog of uridine. A field-desorption mass spectrum (molecular ion at m/e 658) and thin-layer chromatography of the white solid confirmed that it was such tetrabenzoyl derivative.

To a solution of the tetrabenzoyl derivative (3.165 g.) in hot ethanol (328 ml.) was added water (164 ml.) and 1 N hydrochloric acid (18 ml.). This solution was heated under reflux for 20 hr., cooled to room temperature, and concentrated under reduced pressure to remove ethanol. The resulting mixture was filtered to separate a crystalline solid that was then washed thoroughly with water and dried under reduced pressure at 56°: weight, 2.64 g. (96% yield); m.p. 188°–191°. Thin-layer chromatography showed that the solid was the desired tribenzoate containing a trace quantity of the tetrabenzoyl derivative. Recrystallization of this material from ethanol furnished the tribenzoate of the carbocyclic analog of uridine: weight, 2.04 g.; m.p. 191°–194°.

A stirred solution (protected from atmospheric moisture) of 9.1 grams of the tribenzoate of the carbocyclic analog of uridine, thionyl chloride (13.1 ml.), dimethylformamide (762 mg), and chloroform (83 ml.) was boiled under reflux for 6 hr. The reaction solution was cooled to room temperature and concentrated under reduced pressure to a solid, which was dissolved in chloroform (200 ml.). The chloroform solution was extracted with three 40-ml. portions of water, dried with magnesium sulfate, treated with activated charcoal, filtered, and concentrated under reduced pressure to a solid (the 4-chloro-2(1H)-pyrimidinone derivative), which weighed 9.4 g. after it had been stored in a high vacuum overnight to complete the removal of volatile materials. A mixture of the solid and a solution of anhydrous ammonia in methanol (150 ml. of 50% ammonia-methanol) was heated in a stainless steel bomb at 100° for 18 hr. The bomb was cooled and opened, the volatile components of the reaction mixture were evaporated with a current of nitrogen, and the residue was dissolved in water (200 ml.). The water solution was extracted with three 50-ml. portions ethyl acetate to remove benzamide. The aqueous solution was concentrated to remove a small amount of ethyl acetate and then poured onto a column of an acidic ion-exchange resin (50 g. of Amberlite CG-120, H+ form). Water (about 400 ml.) was passed through the column until the neutral components were washed off. The column was then eluted with 2 N aqueous ammonia (300 ml.), and fractions containing the carbocyclic analog of cytidine were located with an ultraviolet monitor and by thin-layer chromatography. These fractions were combined and concentrated under reduced pressure to a solid residue. The solid was triturated with cold water (10 ml.), collected by filtration, and recrystallized from water: weight, 2.18 g (55% yield) of the carbocyclic analog of cytidine: ultraviolet absorption maxima in nanometers at 284 ($\epsilon$ 13500) and 214 ($\epsilon$ 10000) at pH 1; 274 ($\epsilon$ 9300) and 225–230 (shoulder) at pH 7; 275 ($\epsilon$ 9300) and 225–230 (shoulder) at pH 13; mass spectral peaks (M=the molecular ion) at m/e 242 (M+1), 241 (M), 224 (M - OH), 223 (M - H$_2$O), 210 (M - CH$_2$OH), 182, 166, 138, 112; infrared spectrum (1800–1300 cm$^{-1}$ region): 1665, 1620 (broad), 1570 (shoulder), 1520, 1490, 1455, 1400, 1370, 1340, 1330 (shoulder), 1305; $^{13}$C-nuclear magnetic resonance spectrum in dimethylsulroxide-D$_6$ ($\delta$ in parts per million from tetramethylsilane): 28.43, 44.95, 61.54, 62.90, 71.73, 73.50, 93.52, 143.32, 156.28, 165.25.

Analysis. Calcd. for C$_{10}$H$_{15}$N$_3$O$_4$: C, 49.78; H, 6.27; N, 17.42. Found: C, 49.91; H, 6.57; N, 17.60.

Specimens of the carbocyclic analog of cytidine sometimes contained small amounts of the carbocyclic analog of N, N-dimethylcytidine. The source of the dimethylamino substituent was evidently the dimethylformamide used in the preparation of the 4-chloropyrimidinone derivative. The N, N-dimethylcytidine analog was usually not detectable when a chloroform solution of the 4-chloropyrimidinone was washed with water. When small amounts of the N, N-dimethylcytidine analog are present, it may be removed by recrystallization or by chromatography on a cation-exchange resin (sulfonic acid type, analytical grade) in the pyridine salt form. Washing the column with 0.1 M pyridinium formate first elutes the N, N-dimethylcytidine analog and, then, the cytidine analog. The course of the elution may be followed by an ultraviolet monitor or by thin-layer chromatography. Concentration of the appropriate eluate fractions to dryness furnishes the pure cytidine analogs.

EXAMPLE 2

The Carbocyclic Analog of N, N-Dimethylcytidine (Formula IV, R$_1$=R$_2$=CH$_3$; X=Y=OH)

Aqueous solutions containing the carbocyclic analog of N, N-dimethylcytidine may be obtained, as described in Example 1, either by ion-exchange chromatography of specimens of the carbocyclic analog of cytidine containing small amounts of the N, N-dimethylcytidine analog or from filtrates resulting from the recrystallization of the cytidine analog. Lyophilization of an aqueous solution obtained by ion-exchange chromatography, dissolution of the residue in methanol and subsequent evaporation of the methanol, and trituration of the residue with ethyl acetate afforded white crystalline carbocyclic analog of N, N-dimethylcytidine: m.p. 198°–200° with decomposition; ultraviolet absorption maxima (in nanometers): 292 ($\epsilon$ 16600) and 222 ($\epsilon$ 9100) at pH 1, 283 ($\epsilon$ 13500) and shoulders near 240 and 220 at pH 13; infrared spectrum (1800–1300 cm$^{-1}$ region): 1635, 1530, 1500, 1475, 1425, 1400, 1395, 1325 (shoulder), 1315; mass spectral peaks (M=the molecular ion) at m/e 269 (M), 252 (M-OH), 251 (M-H$_2$O), 241 (M-CO), 238 (M-CH$_2$OH), 166 (dimethylaminocytosinyl group+C$_2$H$_4$), 140 (dimethylaminocytosinyl group+2H).

Analysis. Calcd. for C$_{12}$H$_{19}$N$_3$O$_4$.0.25H$_2$O: C, 52.63; H, 7.18, N, 15.35. Found: C, 52.37; H, 7.17; N, 15.34.

The carbocyclic analog of N, N-dimethylcytidine may also be prepared by treating the 4-chloro-2(1$\underline{H}$)-pyrimidinone derivative described in Example 1 with dimethylamine.

EXAMPLE 3

The Carbocyclic Analog of 3'-Deoxycytidine (Formula IV, R$_1$=R$_2$=Y=H; X=OH)

A solution of benzoyl chloride (5.8 g.) in anhydrous pyridine (31.5 ml.) was added dropwise to a stirred solution of 1-[(1$\alpha$, 2$\beta$, 4$\alpha$)-($\pm$)-2-hydroxy-4-(hydroxymethyl)cyclopentyl]-2, 4(1$\underline{H}$, 3$\underline{H}$)-pyrimidinedione (Formula VII, R=Y=H, X=OH; the carbocyclic analog of 3'-deoxyuridine) (2.826 g.) in anhydrous pyridine (63 ml.). The solutions of the reactants and the reaction mixture were protected from atmospheric moisture, and the reaction mixture was stirred. The reaction was exothermic; after the reaction had subsided, the reaction solution was heated 58°–60° for 48 hr. The reaction solution was treated with activated charcoal and filtered, and the filtrate, including the pyridine washings (25 ml.) of the reaction vessel and the charcoal, was poured slowly into a water-ice mixture (1250 ml.). After the ice had melted, the mixture was filtered to separate the precipitate, which was washed thoroughly with water and dried under reduced pressure at room temperature: weight, 6.62 g. (98% yield, calculated as the tribenzoyl derivative of the carbocyclic analog of 3'-deoxyuridine). This material was shown to be predominantly such tribenzoyl derivative by thin-layer chromatography and by mass spectral analysis.

A solution of the tribenzoyl derivative (6.6 g.), ethanol (225 ml.), water (185 ml.), and 1 N hydrochloric acid (21.5 ml.) was boiled under reflux for 32 hr., cooled to room temperature, and concentrated under reduced pressure to remove ethanol. The resulting mixture was chilled and filtered to separate the precipitate, which was washed thoroughly with water and dried under reduced pressure: weight, 4.91 g. (90% yield). A hot solution of this material in ethanol (250 ml.) was treated with activated carbon, filtered, and cooled. The white crystalline dibenzoate was separated by filtration, washed with ethanol, and dried under reduced pressure at 56°; weight, 2.78 g.; m.p. 180°–183°.

A stirred solution (protected from atmospheric moisture) of the above prepared dibenzoate (526 mg.), thionyl chloride (0.97 ml.), dimethylformamide (57 mg.), and chloroform (6 ml.) was boiled under reflux for 6 hr. The reaction solution was cooled to room temperature and concentrated under reduced pressure, and the solid residue was stored in a high vacuum (oil pump) overnight to complete the removal of volatile materials. The mass spectrum of the solid showed that it was predominantly the desired 4-chloro-2(1$\underline{H}$)-pyrimidinone derivative.

A mixture of the 4-chloro-2(1$\underline{H}$)-pyrimidinone derivative and a solution of anhydrous ammonia in methanol (30 ml. of 50% ammonia-methanol) was heated in a stainless steel bomb at 100° for 18 hr. The bomb was cooled and opened, the volatile components of the reaction mixture were evaporated with a current of nitrogen, and the residue was dissolved in water (20 ml.). The water solution was extracted with three 25-ml. portions of ethyl acetate to remove benzamide. The aqueous layer was concentrated to remove a small amount of ethyl acetate and then poured onto a column of an acidic ion-exchange resin (50 ml. of Amberlite CG-120, H+ form). Water was passed through the column until the neutral, ultraviolet-absorbing components were washed off. The column was then eluted with 0.5 N aqueous ammonia, and the product-containing eluate (located with an ultraviolet monitor) was concentrated under reduced pressure to a colorless syrup (weight, 213 mg.). Trituration of the syrup with an ether-methanol (9:1) mixture afforded the carbocyclic analog of 3'-deoxycytidine as a white crystalline solid: weight, 187 mg. (69% yield from the dibenzoate).

The carbocyclic analog of 3'-deoxycytidine prepared from unpurified 4-chloro-2(1$\underline{H}$)-pyrimidinone derivative sometimes contained a trace amount of the analogous N, N-dimethylcytosine derivative, detectable by mass spectral analysis or by thin-layer chromatography. The carbocyclic analog of 3'-deoxycytidine may be purified further, if desired, by ion exchange chromatography as illustrated below. A solution of the carbocyclic analog (487 mg.) of 3'-deoxycytidine, prepared as described above, in water (25 ml.) was poured onto a column (50 ml.) of a cation-exchange resin (sulfonic acid type, analytical grade) in the pyridine salt form. Washing the column with 0.1 M pyridinium formate first elutes the N, N-dimethylcytosine derivative and, then, the carbocyclic analog of 3'-deoxycytidine. The course of the elution may be followed with an ultraviolet monitor or by thin-layer chromatography. Concentration to dryness of the eluate solution containing the carbocyclic analog of 3'-deoxycytidine, trituration of the residue with acetonitrile, and recrystallization of the resulting solid from methanol gave pure carbocyclic analog of 3'-deoxycytidine (254 mg.): m.p. 211°–214° with decomposition; ultraviolet absorption maxima (in nanometers) at 285 ($\epsilon$ 13200) and 214 ($\epsilon$ 10,000) at pH 1, 275 ($\epsilon$ 9100) and 225–230 (shoulder) at pH 7, 275 ($\epsilon$ 9000) and 225–230 (shoulder) at pH 13; mass spectral peaks (M=the molecular ion) at m/e 226 (M+1), 225 (M), 208 (M - OH), 207 (M - H$_2$O), 197 (M - CO), 196, 194 (M - CH$_2$OH), 176, 166, 138 (cytosinyl group+C$_2$H$_4$), 112 (cytosinyl+2H); proton NMR spectrum in dimethylsulfoxide-D$_6$ ($\delta$ in parts per million from tetramethylsilane): 0.92–2.4 (multiplet due to CH$_2$, CH, CH$_2$ at positions 3, 4, and 5 of the cyclopentane ring), 3.33 (approximate doublet due to CH$_2$ of CH$_2$OH), 3.9–4.28 (multiplet due to CH at position 2 of cyclopentane ring), 4.3–4.68 (multiplet due to OH of CH$_2$OH and CH at position 1 of cyclopentane ring), 4.92 (approximate doublet due to OH at position 2 of cyclopentane ring), 5.7 (doublet due to H at position 5 of pyrimidine ring), 6.96 (NH$_2$), 7.58 (doublet due to H at position 6 of pyrimidine ring).

Analysis. Calcd. C$_{10}$H$_{15}$N$_3$O$_3$: C, 53.32; H, 6.71; N, 18.65. Found: C, 52.92; H, 6.79; N, 18.89.

EXAMPLE 4

The Carbocyclic Analog of 2'-Deoxycytidine (Formula IV, R$_1$=R$_2$=X=H; Y=OH)

The carbocyclic analog of 2'-deoxyuridine (Formula VII, R=X=H, Y=OH) was treated with benzoyl chloride in pyridine according to the procedure described in Example 3. A gummy precipitate separated when the reaction solution was poured into a water-ice mixture. The precipitate was separated partly by decantation and partly by filtration of the aqueous phase and was dissolved in chloroform. The chloroform solution was washed with 0.5 N hydrochloric acid and, then, with aqueous sodium bicarbonate solution, dried with magnesium sulfate, treated with activated charcoal, and concentrated to dryness under reduced pressure. The white residue was shown by thin-layer chromatography and by mass spectral analysis to be the tribenzoyl derivative of the carbocyclic analog of 2'-deoxyuridine. The material (3.73 g.) obtained in this way from 1.653 g. of the carbocyclic analog of 2'-deoxyuridine was dissolved in a solution of 120 ml. of ethanol, 120 ml. of water, and 12.5 ml. of 1 N hydrochloric acid; this solution was boiled under reflux for 15 hr. and concentrated under reduced pressure to remove some of the ethanol; and the resulting mixture was diluted with water (60 ml.) and chilled. A white precipitate (the dibenzoate of the carbocyclic analog of 2'-deoxyuridine) was separated by filtration, washed well with water, and dried under reduced pressure at 56°; weight, 2.687 g. (85% yield); m.p. 189°–193°. Recrystallization of this product from ethanol furnished white platelets: weight, 2.26 g.; m.p. 192°–194°.

The dibenzoate of the carbocyclic analog of 2'-deoxyuridine was converted to the 4-chloro-2(1$\underline{H}$)-pyrimidinone derivative, which in turn was converted to the carbocyclic analog of 2'-deoxycytidine by the procedure described in Example 3. The aqueous layer obtained after extraction of benzamide with ethyl acetate was concentrated to dryness under reduced pressure. The residual solid was chromatographed on a column of a cation-exchange resin (sulfonic acid type, analytical grade) in the pyridine salt form to separate the carbocyclic analog of N, N-dimethyl-2'-deoxycytidine. The column was eluted with 0.1 M pyridinium formate solution, and the course of the elution as followed with an ultraviolet monitor. For example, the crude product obtained from 2.7 g. of the dibenzoate was subjected to ion-exchange chromatography, and 130 fractions of eluate of approximately 25 ml., each, were collected. Fractions 75 through 124 (selected by the ultraviolet monitoring of the effluent) were combined and concentrated to a residual oil, which was placed in a high vacuum at 50° to remove additional volatile material. Methanol (three 10-ml. portions) was added to and evaporated from the solid product, and the resulting solid was then triturated with acetonitrile, collected by filtration, and dried. A solution of the resulting solid (998 mg.) in concentrated aqueous ammonia (50 ml.) was boiled under reflux for 1.5 hr. (to hydrolyze a small amount of a formyl derivative), and then concentrated to dryness under reduced pressure to a white solid (859 mg.). A water solution of 850 mg. of the residual solid was poured onto a column of a basic ion-exchange resin (quaternary ammonium type, hydroxide form, research grade), and the column was eluted further with water. The eluate was concentrated to dryness under reduced pressure, and the white solid residue was dried further under reduced pressure at 56° for 2 hr. and at 110° overnight: weight, 725 mg. (52% yield); m.p. 215°–217°; ultraviolet absorption maxima (in nanometers) at 284 ($\epsilon$ 13800) and 214 ($\epsilon$ 10400) at pH 1, 2.75 ($\epsilon$ 9500) and 225–230 (shoulder) at pH 7 and at pH 13; mass spectral peaks (M=the molecular ion) at m/e 22(M), 208(M-OH), 194(M-CH$_2$OH), 178, 176, 151, 138 (cytosinyl group+C$_2$H$_4$), 112 (cytosinyl group+2$\underline{H}$); proton NMR spectrum in dimethylsulfoxide-D$_6$ ($\delta$ in parts per million from tetramethylsilane); ca. 1–2.3 (multiplet due to CH$_2$, CH, CH$_2$ at positions 2, 4, and 5 of the cyclopentane ring), 3.2–3.6 (multiplet due to CH$_2$ of CH$_2$OH), 3.84–4.1 (multiplet due to CH at position 3 of the cyclopentane ring), 4.44–4.74 (overlapping multiplet due to OH of CH$_2$OH and OH at position 3 of the cyclopentane ring), 4.78–5.2 (multiplet due to CH at position 1 of the cyclopentane ring), 5.7 (doublet due to H at position 5 of pyrimidine ring), 6.94 (NH$_2$), 7.6 (doublet due to H at position 6 of the pyrimidine ring); infrared spectrum (1800–1300 cm$^{-1}$ region): 1645, 1630 (shoulder), 1585, 1570, 1520, 1480 (shoulder), 1470, 1395, 1360, 1300.

Analysis. Calcd. for C$_{10}$H$_{15}$N$_3$O$_3$: C, 53.33; H, 6.71; N, 18.66. Found: C, 53.24; H, 6.40; N, 18.87.

Fractions 50–59 obtained from the column of the cation-exchange resin (sulfonic acid type) described above were combined and concentrated to dryness under reduced pressure. The mass spectrum of the residual solid included the following peaks (M=the molecular ion) and showed that it was the carbocyclic analog of N,N-dimethyl-2'-deoxycytidine (Formula IV, R$_1$=R$_2$=CH$_3$; X=H; Y=OH): m/e 253(M), 236(M-OH) 222(M-CH$_2$OH), 166 (dimethylcytosinyl group+C$_2$H$_4$), 140 (dimethylcytosinyl group+2H).

EXAMPLE 5

The Carbocyclic Analogs of O$^2$, 2'-Cyclocytidine (Formula VI, Y=OH) and of 1-$\beta$-Arabinofuranosylcytosine (Formula V, R$_1$=R$_2$=H; X=Y=OH)

Part A. Thionyl chloride (0.375 ml.) was added to redistilled dimethylformamide (2.5 ml.); and, after an exothermic reaction had subsided, the solution (protected from atmospheric moisture) was stirred at room temperature for 0.5 hr. The carbocyclic analog (250 mg.) of cytidine (Example 1) was then added to this solution. After the exothermic reaction had subsided, the reaction solution was stirred at room temperature for 3 hr., and water (6.25 ml.) was then added. The resulting solution was sparged with nitrogen to remove dissolved sulfur dioxide, and the solution was concentrated under reduced pressure to a gummy residue. After several portions of water had been added to and evaporated from the residue, it was chromatographed in 0.1 M pyridinium formate on a column (25×2 cm.) of a cation-exchange resin (sulfonic acid type, analytical grade) in the pyridine salt form. Elution of the column with 0.1 M pyridinium formate furnished eluate portions (which were located by ultraviolet monitoring of the effluent) containing the carbocyclic analog of O$^2$, 2'-cyclocytidine. These fractions were combined and lyophilized. The residue was dissolved in water, the solution was filtered, and the filtrate was lyophilized. The residual white solid was characterized by its mass and nuclear magnetic resonance spectra as the carbocyclic analog of O$^2$, 2'-cyclocytidine; mass spectral peaks (M=the molecular ion) at m/e 223 (M), 206 (M-OH), 192 (M-CH$_2$OH); nuclear magnetic resonance spectrum in dimethylsulfoxide-D$_6$ ($\delta$ in parts per million from tetramethylsilane); 1.5–2.24 (multiplet due to CH$_2$ at position 5 of the cyclopentane ring), 2.24–2.6 (multiplet due to CH at position 4 of the cyclopentane ring), 3.3–3.5 (multiplet due to CH$_2$ of CH$_2$OH), 3.9–4.16 (multiplet due to CH at position 3 of the cyclopentane ring), 4.9–5.4 (overlapping multiplet due to CH at positions 1 and 2 of the cyclopentane ring, position 1 being the point of attachment of the pyrimidine-ring nitrogen), 6.65 (center of doublet due to H at position 5 of the pyrimidine ring), 8.24 (center of doublet due to H at position 6 of the pyrimidine ring), broad NH and OH multiplets.

A solution of the carbocyclic analog (110 mg.) of O$^2$, 2'-cyclocytidine in 1 N aqueous ammonia (12 ml.) was boiled under reflux for 15 min. and then concentrated to dryness under reduced pressure. Dissolution of the white residual solid in hot ethanol and chilling the solution caused precipitation of the carbocyclic analog of 1-$\beta$-arabinofuranosylcytosine; yield, 78 mg. (66%); m.p. 225°–227° with decomposition; ultraviolet absorption maxima (in nanometers) at 284 ($\epsilon$ 13800) and 214 ($\epsilon$ 10100) at pH 1, 275 ($\epsilon$ 9500) and 225–230 (shoulder) at pH 7, 275 ($\epsilon$ 9700) and 225–230 (shoulder) at pH 13; mass spectral peaks (M=the molecular ion) at m/e 242 (M+1), 241 (M), 224 (M-OH), 223 (M-H$_2$O), 182, 166, 138, 112; proton nuclear magnetic resonance spectrum in DMSO-D$_6$ ($\delta$ in parts per million from tetramethylsilane): 1.5–2.0 (multiplet due to CH$_2$ and CH at positions 4 and 5 of the cyclopentane ring), 3.26–3.7 (overlapping multiplet due to CH$_2$ of CH$_2$OH and H at position 3 of the cyclopentane ring), 3.7–3.86 (multiplet due to CH at position 2 of the cyclopentane ring), 4.46–4.7 (multiplet due to OH of CH$_2$OH), 4.7–5.1 (multiplet due to H at position 1 and OH at positions 2 and 3 of the cyclopentane ring), 5.63 (center of doublet due to H at position 5 of the pyrimidine ring), 7.55 (center of doublet due to H at position 6 of the pyrimidine ring). The carbocyclic analog of 1-$\beta$-arabinofuranosylcytosine moved slightly faster than the carbocyclic analog of cytidine on a thin-layer plate of silica gel with 2-propanol-water-concentrated aqueous ammonia (8:1:1) as solvent.

Analysis. Calcd. for C$_{10}$H$_{15}$N$_3$O$_4$: C, 49.78; H, 6.27; N, 17.42. Found: C, 49.43; H, 6.37; N, 17.54

Part B. A mixture of 2-acetoxybenzoyl chloride (594 mg.), anhydrous acetonitrile (2.2 ml.), and the carbocyclic analog of cytidine (594 mg.) was boiled under reflux for about 20 min., cooled to room temperature, and filtered. The filtrate was concentrated under reduced pressure to a syrup which was dissolved in acetone (3 ml.). The acetone solution was stored at low temperature, and a white crystalline precipitate was collected by filtration, washed with cold acetone, and dried under reduced pressure at 56°. The mass spectrum of this material showed that it was the diacetyl derivative of the carbocyclic analog of cyclocytidine hydrochloride (M=the molecular ion): m/e 307 (M), 264 (M-acetyl), 248 (M-acetoxy), 234 (M-CH$_2$OCOCH$_3$), 36.

A solution of the diacetyl derivative (30 mg.) of the carbocyclic analog of cyclocytidine, described immediately above, in methanol (15 ml.) saturated with hydrogen chloride was stirred at room temperature overnight. Evaporation of volatile components with a stream of nitrogen, then under reduced pressure, and in a high vacuum left the hydrochloride of the carbocyclic analog of cyclocytidine (30 mg.); the mass spectrum included the expected peaks (m/e 223, 206, 192). A solution of this material in 1 N aqueous ammonia (2 ml.) was heated at 80°–85° for 5 min. Volatile components were evaporated under reduced pressure and, then, in a high vacuum. Crystallization of the residue from ethanol gave the carbocyclic analog of 1-$\beta$-arabinofuranosylcytosine. This compound may also be isolated by ion-exchange chromatography, by preparative thin-layer chromatography, or by the sequential use of these techniques after impure preparations containing the carbocyclic analog of cyclocytidine are treated with aqueous ammonia. The properties of the pure compound prepared by the procedure of either Part A or Part B are summarized in Part A.

EXAMPLE 6

The Carbocyclic Analogs of 3'-Deoxy-$0^2$, 2'-Cyclocytidine (Formula VI, Y=H) and of 3'-Deoxy-1-β-arabinofuranosylcytosine (Formula V, $R_1=R_2=Y=H$; X=OH)

The carbocyclic analog of 3'-deoxycytidine (Example 3) was treated with the thionyl chloride-dimethylformamide reagent according to the procedure described in Part A of Example 5. The carbocyclic analog of 3'-deoxy-$0^2$, 2'-cyclocytidine was isolated similarly in 63% yield: m.p. 151°–154° with decomposition; mass spectral peaks (M=the molecular ion) at m/e 207 (M), 176 (M-$CH_2OH$); nuclear magnetic resonance spectrum in dimethylsulfoxide-$D_6$ (δ in parts per million from tetramethylsilane): 1.6–2.5 (multiplet due to $CH_2$, $CH_2$, CH at positions 3, 4, and 5 of the cyclopentane ring), 3–3.4 (multiplet due to $CH_2$ of $CH_2OH$), 4.9–5.2 and 5.4–5.7 (multiplets due to CH at positions 1 and 2 of the cyclopentane ring, position 1 being the point of attachment of the pyrimidine ring nitrogen), 6.68 (center of doublet due to H at position 5 of the pyrimidine ring), 8.21 (center of doublet due to H at position 6 of the pyrimidine ring), 8.55 (singlet due to NH); infrared spectrum (1800–1400 cm$^{-1}$ region): 1655, 1590, 1495, 1440, 1415.

Analysis. Calcd. for $C_{10}H_{13}N_3O_2$.1.25 HCOOH: C, 51.03; H, 5.90; N, 15.87. Found: C, 51.18; H, 5.86; N, 16.52.

The carbocyclic analog of 3'-deoxy-1-β-arabinofuranosylcytosine was obtained by heating the carbocyclic analog of 3'-deoxy-$0^2$, 2'-cyclocytidine with 1 N aqueous ammonia at 80° for 5 min. and evaporating the volatile material under reduced pressure. The mass spectrum of the residual white solid included peaks (M=the molecular ion) at m/e 225 (M), 208 (M-OH), 207 (M-$H_2O$), 196, 176, 166, 138 (cytosinyl group+$C_2H_4$), 112 (cytosinyl group+2H). The carbocyclic analog of 3'-deoxy-1-β-arabinofuranosylcytosine moved slightly faster than the carbocyclic analog of 3'-deoxycytidine on a thin-layer plate of silica gel with 2-propanol-water-concentrated aqueous ammonia (7:2:1) as solvent; its retention time on a high pressure liquid chromatographic column (octadecylsilane-bonded silica) with water-acetonitrile (98:2) as solvent was greater than that of the 3'-deoxycytidine analog.

EXAMPLE 7

The carbocyclic analog of cytidine (Example 1) and the carbocyclic analog of 1-β-arabinofuranosylcytosine (Example 5) were tested for antiviral activity against selected viruses that replicate in cells in cell culture. The results of these tests are summarized in Table 1 below. The Virus Rating (VR) is a weighted measurement of antiviral activity determined by a modification of the method of Ehrlich et al., Annals of the New York Academy of Science, 130, 5 (1965). In these tests, a VR of 0.5–0.9 indicates marginal to moderate antiviral activity and a VR equal to or greater than 1.0 indicates definite antiviral activity. The higher the value of VR, the greater is the antiviral activity.

TABLE 1

| | Antiviral Activity of Carbocyclic Analogs of Cytosine Nucleosides, Average Virus Rating (VR) | | | | |
|---|---|---|---|---|---|
| | DNA Viruses | | RNA Viruses | | |
| Compound | Herpes Simplex Virus Type 1 | Vacccinia Virus | Rhinovirus Type IA | Influenza Ao/ PR8/34 | Influenza A2/Aichi/ 2/68 |
| Carbocyclic Analog of Cytidine | 0.8 | 0.9 | 0.7 | 3.0 | 2.6 |
| Carbocyclic Analog of 1-β-arabino-furanosylcytosine | 0.6 | — | 0.7 | — | — |

The above tests show that the carbocyclic analog of cytidine and the carbocyclic analog of 1-β-arabinofuranosylcytosine inhibit the replication of both DNA and RNA viruses. Of particular importance is the high activity of the carbocyclic analog of cytidine against influenza virus. This activity is in marked contrast to the lack of activity of 1-β-D-arabinofuranosylcytosine (Ara-C) against influenza virus, as indicated by Creasey, "Arabinosylcytosine", in Antineoplastic and Immunosuppressive Agents, Part II, chapter 42, Sartorelli and Johns, Editors, Springer-Verlag, New York, N.Y., 1975; Prince et al, Proceedings of the Society for Experimental Biology and Medicine, Volume 130, pages 1080–1086 (1969); and Sidewell et al, Applied Microbiology, Volume 16, pages 370–392 (1968). Thus, the carbocyclic analog of cytidine is highly active against one of the most important human viruses; whereas Ara-C, a cytosine nucleoside, does not demonstrate this activity.

EXAMPLE 8

The carbocyclic analog of cytidine (Example 1) was also tested for its antineoplastic activity against the L-1210 mouse leukemia test system. The results are summarized in Table 2 below.

TABLE 2

| Antileukemic Activity of the Carbocyclic Analog of Cytidine in Mice with Leukemia L1210 | | | |
|---|---|---|---|
| | Average Survival Time in Days | | % Increase in Survival |
| Dose in mg./kg./dose* | Treated Mice | Control Mice | Time of Treated Mice |
| 450 | 14.8 | 8.9 | 66 |
| 300 | 13.3 | 8.9 | 49 |
| 200 | 17.0 | 9.3 | 82 |
| 150 | 14.0 | 9.3 | 50 |
| 100 | 12.7 | 9.3 | 36 |
| 100 | 13.0 | 8.5 | 52 |

*All doses were administered daily for nine days beginning on the day following innoculation of the mice with $10^5$ leukemia cells.

The above results indicate that the carbocyclic analog of cytidine inhibits L1210 leukemia in mice. The survival time of mice bearing L1210 leukemia and treated with the carbocyclic analog of cytidine was about 60% greater than the survival time of untreated leukemic mice.

The embodiments of the invention in which an exclusive property or privilege is claimed are defined as follows:

1. A compound having the formula

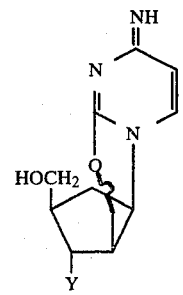

wherein Y is hydrogen or hydroxy.

* * * * *